(12) United States Patent
O'Neill et al.

(10) Patent No.: US 8,632,841 B2
(45) Date of Patent: Jan. 21, 2014

(54) SYSTEMS AND METHODS FOR ROTATING AND COATING AN IMPLANTABLE DEVICE

(71) Applicant: Abbott Cardiovascular Systems, Inc., Santa Clara, CA (US)

(72) Inventors: David O'Neill, Galway (IE); Mathew Coates, Boston, MA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 13/781,249

(22) Filed: Feb. 28, 2013

(65) Prior Publication Data
US 2013/0177696 A1    Jul. 11, 2013

Related U.S. Application Data

(63) Continuation of application No. 12/817,544, filed on Jun. 17, 2010, now Pat. No. 8,389,041.

(51) Int. Cl.
| | | |
|---|---|---|
| *A61L 33/00* | (2006.01) | |
| *B05D 3/00* | (2006.01) | |
| *B05D 7/00* | (2006.01) | |
| *B23Q 3/00* | (2006.01) | |

(52) U.S. Cl.
USPC .................. 427/2.1; 427/2.25; 269/289 R (58) Field of Classification Search
USPC ................. 427/2.1, 2.25; 269/289 R
See application file for complete search history.

(56) References Cited

U.S. PATENT DOCUMENTS

| | | |
|---|---|---|
| 4,322,398 A | 3/1982 | Reiner et al. |
| 4,324,812 A | 4/1982 | Bentley |
| 4,580,568 A | 4/1986 | Gianturco |
| 4,733,665 A | 3/1988 | Palmaz |
| 4,877,745 A | 10/1989 | Hayes et al. |
| 5,246,530 A | 9/1993 | Bugle et al. |
| 5,464,650 A | 11/1995 | Berg et al. |
| 5,591,227 A | 1/1997 | Dinh et al. |

(Continued)

FOREIGN PATENT DOCUMENTS

| | | |
|---|---|---|
| DE | 19940241 | 3/2001 |
| DE | 19940242 | 3/2001 |

(Continued)

OTHER PUBLICATIONS

U.S. Appl. No. 60/424,574, filed Nov. 7, 2002, Cromack.

(Continued)

*Primary Examiner* — Timothy Vanoy
(74) *Attorney, Agent, or Firm* — Workman Nydegger; Ron Devore (57) ABSTRACT

A method for applying a coating to an implantable device is disclosed. The method includes positioning an implantable device relative to an ultrasonic material delivery apparatus. The implantable device is rotated at a relative speed. The relative speed may be more than 120 revolutions per minute. An application material is applied to the implantable device using the ultrasonic material delivery apparatus. The relative speed may be sufficient to reduce the size of at least a portion of droplets of the application material. A system for rotating an implantable device is disclosed. The system includes an implantable device and a rotation system configured to rotate the implantable device. A longitudinal axis of the implantable device and a longitudinal axis of a rotation member of the rotation system may be offset a desired dimension. An inside diameter of the implantable device may be larger than an outside diameter of a rotation member.

15 Claims, 4 Drawing Sheets

(56) References Cited

U.S. PATENT DOCUMENTS

| | | | |
|---|---|---|---|
| 5,605,696 A | 2/1997 | Eury et al. |
| 5,644,391 A | 7/1997 | Grego et al. |
| 5,649,977 A | 7/1997 | Campbell |
| 5,667,840 A | 9/1997 | Tingey et al. |
| 5,705,583 A | 1/1998 | Bowers et al. |
| 5,741,429 A | 4/1998 | Donadio, III et al. |
| 5,755,771 A | 5/1998 | Penn et al. |
| 5,820,917 A | 10/1998 | Tuch |
| 5,820,918 A | 10/1998 | Ronan et al. |
| 5,824,048 A | 10/1998 | Tuch |
| 5,824,049 A | 10/1998 | Ragheb et al. |
| 5,830,396 A | 11/1998 | Higgins et al. |
| 5,833,891 A | 11/1998 | Subramaniam et al. |
| 5,837,313 A | 11/1998 | Ding et al. |
| 5,873,904 A | 2/1999 | Ragheb et al. |
| 5,906,682 A | 5/1999 | Bouras et al. |
| 5,951,586 A | 9/1999 | Berg et al. |
| 5,972,027 A | 10/1999 | Johnson |
| 5,980,972 A | 11/1999 | Ding |
| 6,015,815 A | 1/2000 | Mollison |
| 6,027,863 A | 2/2000 | Donadio, III |
| 6,033,434 A | 3/2000 | Borghi |
| 6,083,257 A | 7/2000 | Taylor et al. |
| 6,086,942 A | 7/2000 | Carden, Jr. et al. |
| 6,090,901 A | 7/2000 | Bowers et al. |
| 6,096,070 A | 8/2000 | Ragheb et al. |
| 6,099,562 A | 8/2000 | Ding et al. |
| 6,106,548 A | 8/2000 | Roubin et al. |
| 6,107,004 A | 8/2000 | Donadio, III |
| 6,121,027 A | 9/2000 | Clapper et al. |
| 6,153,252 A | 11/2000 | Hossainy et al. |
| 6,187,322 B1 | 2/2001 | Hille et al. |
| 6,209,621 B1 | 4/2001 | Treacy |
| 6,231,600 B1 | 5/2001 | Zhong |
| 6,240,616 B1 | 6/2001 | Yan |
| 6,251,136 B1 | 6/2001 | Guruwaiya et al. |
| 6,254,634 B1 | 7/2001 | Anderson et al. |
| 6,258,371 B1 | 7/2001 | Koulik et al. |
| 6,273,913 B1 | 8/2001 | Wright et al. |
| 6,287,332 B1 | 9/2001 | Bolz et al. |
| 6,296,708 B1 | 10/2001 | Coulibaly et al. |
| 6,299,604 B1 | 10/2001 | Ragheb et al. |
| 6,319,277 B1 | 11/2001 | Rudnick et al. |
| 6,329,386 B1 | 12/2001 | Mollison |
| 6,335,029 B1 | 1/2002 | Kamath et al. |
| 6,358,556 B1 | 3/2002 | Ding et al. |
| 6,379,379 B1 | 4/2002 | Wang |
| 6,387,121 B1 | 5/2002 | Alt |
| 6,395,326 B1 | 5/2002 | Castro et al. |
| 6,409,716 B1 | 6/2002 | Sahatjian et al. |
| 6,488,701 B1 | 12/2002 | Nolting et al. |
| 6,506,437 B1 | 1/2003 | Harish et al. |
| 6,519,568 B1 | 2/2003 | Harvey et al. |
| 6,521,658 B1 | 2/2003 | Li et al. |
| 6,558,733 B1 | 5/2003 | Hossainy et al. |
| 6,574,851 B1 | 6/2003 | Mirizzi |
| 6,599,516 B1 | 7/2003 | Knaack |
| 6,616,765 B1 | 9/2003 | Castro et al. |
| 6,627,246 B2 | 9/2003 | Mehta et al. |
| 6,645,547 B1 | 11/2003 | Shekalim et al. |
| 6,676,987 B2 | 1/2004 | Zhong et al. |
| 6,699,281 B2 | 3/2004 | Vallana et al. |
| 6,713,119 B2 | 3/2004 | Hossainy et al. |
| 6,743,463 B2 | 6/2004 | Weber et al. |
| 6,808,536 B2 | 10/2004 | Wright et al. |
| 6,901,659 B1 | 6/2005 | Mishima |
| 7,048,962 B2 | 5/2006 | Shekalim et al. |
| 7,083,822 B2 | 8/2006 | Brightbill |
| 7,208,190 B2* | 4/2007 | Verlee et al. ................. 427/2.24 |
| 7,597,764 B2 | 10/2009 | Verlee et al. |
| 7,645,476 B2 | 1/2010 | Verlee et al. |
| 8,001,926 B2 | 8/2011 | Verlee et al. |
| 8,389,041 B2 | 3/2013 | O'Neill et al. |
| 2001/0021873 A1 | 9/2001 | Stinson |
| 2001/0027340 A1 | 10/2001 | Wright et al. |
| 2001/0029351 A1 | 10/2001 | Falotico et al. |
| 2002/0004060 A1 | 1/2002 | Heublein et al. |
| 2002/0051846 A1 | 5/2002 | Kirkpatrick et al. |
| 2002/0111667 A1 | 8/2002 | Girton et al. |
| 2002/0123505 A1 | 9/2002 | Mollison et al. |
| 2002/0183581 A1 | 12/2002 | Yoe et al. |
| 2003/0004564 A1 | 1/2003 | Elkins et al. |
| 2003/0018380 A1 | 1/2003 | Craig et al. |
| 2003/0068355 A1 | 4/2003 | Shanley et al. |
| 2003/0083646 A1 | 5/2003 | Sirhan et al. |
| 2003/0129215 A1 | 7/2003 | Mollison et al. |
| 2003/0185964 A1 | 10/2003 | Weber et al. |
| 2003/0207019 A1 | 11/2003 | Shekalim et al. |
| 2004/0044398 A1 | 3/2004 | Nicholas |
| 2004/0130584 A1 | 7/2004 | Kobayashi et al. |
| 2004/0168171 A1 | 8/2004 | Comparato et al. |
| 2004/0185081 A1 | 9/2004 | Verlee et al. |
| 2004/0254634 A1 | 12/2004 | Verlee et al. |
| 2005/0158449 A1 | 7/2005 | Chappa |
| 2007/0189915 A1 | 8/2007 | Shrivastava et al. |
| 2007/0191943 A1 | 8/2007 | Shrivastava et al. |
| 2008/0020129 A1 | 1/2008 | Verlee et al. |
| 2009/0061072 A1* | 3/2009 | Isch et al. .................. 427/2.25 |
| 2010/0003396 A1 | 1/2010 | Verlee et al. |
| 2010/0262230 A1 | 10/2010 | Vecerina et al. |

FOREIGN PATENT DOCUMENTS

| | | |
|---|---|---|
| EP | 0850651 | 12/1997 |
| JP | 11076278 | 3/1999 |
| WO | WO 97/03654 | 2/1997 |
| WO | WO 97/10011 | 3/1997 |
| WO | WO 98/00107 | 1/1998 |
| WO | WO 98/32474 | 7/1998 |
| WO | WO 01/76525 | 10/2001 |
| WO | WO 01/91918 | 12/2001 |
| WO | WO 02/069848 | 9/2002 |
| WO | WO 2004/022124 | 3/2004 |
| WO | WO 2004/043298 | 5/2004 |
| WO | WO 2004/043299 | 5/2004 |
| WO | WO 2004/043300 | 5/2004 |

OTHER PUBLICATIONS

U.S. Appl. No. 60/424,575, filed Nov. 7, 2002, Clifford.
U.S. Appl. No. 60/424,576, filed Nov. 7, 2002, Cromack et al.
U.S. Appl. No. 60/424,577, filed Nov. 7, 2002, Fisher, Jr. et al.
U.S. Appl. No. 60/424,607, filed Nov. 7, 2002, Verlee et al.
Cooley, et al. "Applications of Ink-Jet Printing Technology to BioMEMS and Microfluidic Systems". Proc. SPIE Conf. on Micreofluidics, Oct. 2001.
Japanese Office Action issued by JPO on Sep. 29, 2009, in connection with Appl. No. 2004-551918, 3 pgs.
Precipitation, FreeOnlineDictionary, pp. 1-4, acessed Oct. 20, 2009 from http://www.thefreedictionary.com/precipitation.
Simamora, Pahala et al., Solubilization of Rapamycin, International Journal of Pharmaceutics, 213 (2001) 25-29.
Sigma, Dexamethasone Crystalline, Mar. 2001, pp. 1-2.
Trécant, Marylène, et al., "Dynamic compaction: a new process to compact therapeutic agent-loaded calcium phosphates," Biomaterials 18 (1997) 141-145.
U.S. Appl. No. 10/703,820, Sep. 8, 2004, Office Action.
U.S. Appl. No. 10/703,820, Jun. 15, 2005, Office Action.
U.S. Appl. No. 10/703,820, May 5, 2006, Notice of Allowance.
U.S. Appl. No. 10/703,891, Dec. 15, 2006, Office Action.
U.S. Appl. No. 10/703,891, Aug. 23, 2007, Notice of Allowance.
U.S. Appl. No. 10/703,891, Jan. 28, 2008, Office Action.
U.S. Appl. No. 10/703,891, Mar. 31, 2008, Office Action.
U.S. Appl. No. 10/703,891, May 20, 2009, Office Action.
U.S. Appl. No. 10/703,891, Nov. 10, 2009, Office Action.
U.S. Appl. No. 10/703,891, Jun. 10, 2010, Office Action.
U.S. Appl. No. 10/703,891, Jun. 2, 2011, Office Action.
U.S. Appl. No. 10/704,069, Oct. 10, 2007, Office Action.
U.S. Appl. No. 10/704,114, Mar. 24, 2005, Office Action.
U.S. Appl. No. 10/704,114, May 3, 2006, Office Action.
U.S. Appl. No. 10/704,114, Aug. 23, 2006, Office Action.

(56) References Cited

OTHER PUBLICATIONS

U.S. Appl. No. 10/704,114, Apr. 9, 2007, Office Action.
U.S. Appl. No. 10/704,114, Jul. 26, 2007, Office Action.
U.S. Appl. No. 10/704,114, Dec. 12, 2007, Office Action.
U.S. Appl. No. 10/704,114, Jun. 26, 2008, Office Action.
U.S. Appl. No. 10/704,114, Jan. 30, 2009, Office Action.
U.S. Appl. No. 10/704,114, Apr. 14, 2009, Office Action.
U.S. Appl. No. 10/704,114, May 28, 2009, Office Action.
U.S. Appl. No. 10/704,114, Dec. 7, 2009, Office Action.
U.S. Appl. No. 10/704,114, Aug. 2, 2010, Office Action.
U.S. Appl. No. 10/704,114, Jan. 18, 2011, Office Action.
U.S. Appl. No. 10/704,114, May 9, 2011, Office Action.
U.S. Appl. No. 10/704,114, Sep. 14, 2011, Office Action.
U.S. Appl. No. 11/465,396, Nov. 15, 2007, Office Action.
U.S. Appl. No. 11/465,396, Jun. 11, 2008, Office Action.
U.S. Appl. No. 11/465,396, Jan. 5, 2009, Office Action.
U.S. Appl. No. 11/465,396, May 26, 2009, Notice of Allowance.
U.S. Appl. No. 11/465,396, Jun. 26, 2009, Notice of Allowance.
U.S. Appl. No. 11/563,283, Jul. 23, 2008, Office Action.
U.S. Appl. No. 11/563,283, Apr. 15, 2009, Office Action.
U.S. Appl. No. 11/563,283, Oct. 26, 2009, Office Action.
U.S. Appl. No. 11/563,283, May 26, 2010, Office Action.
U.S. Appl. No. 11/563,283, Aug. 31, 2010, Office Action.
U.S. Appl. No. 11/563,283, Jun. 20, 2011, Office Action.
U.S. Appl. No. 11/563,283, Nov. 30, 2011, Notice of Allowance.
U.S. Appl. No. 11/563,283, Mar. 20, 2012, Notice of Allowance.
U.S. Appl. No. 11/563,285, Dec. 31, 2008, Office Action.
U.S. Appl. No. 11/563,285, Aug. 10, 2009, Office Action.
U.S. Appl. No. 11/563,285, Jul. 30, 2012, Office Action.
U.S. Appl. No. 11/563,285, Jan. 22, 2013, Office Action.
U.S. Appl. No. 11/738,839, Aug. 6, 2008, Office Action.
U.S. Appl. No. 11/738,839, Feb. 5, 2009, Office Action.
U.S. Appl. No. 11/738,839, Mar. 20, 2009, Office Action.
U.S. Appl. No. 11/738,839, Aug. 28, 2009, Notice of Allowance.
U.S. Appl. No. 12/551,413, Apr. 1, 2010, Office Action.
U.S. Appl. No. 12/551,413, May 27, 2010, Office Action.
U.S. Appl. No. 12/551,413, Nov. 8, 2010, Office Action.
U.S. Appl. No. 12/551,413, Feb. 14, 2011, Office Action.
U.S. Appl. No. 12/551,413, May 2, 2011, Notice of Allowance.
U.S. Appl. No. 12/817,544, Jul. 27, 2012, Office Action.
U.S. Appl. No. 12/817,544, Nov. 9, 2012, Notice of Allowance.
U.S. Appl. No. 11/563,285, May 1, 2013, Notice of Allowance.
U.S. Appl. No. 11/563,285, Aug. 14, 2013, Issue Notification.

* cited by examiner

shows:

SYSTEMS AND METHODS FOR ROTATING AND COATING AN IMPLANTABLE DEVICE

CROSS REFERENCE TO RELATED APPLICATIONS

This application is a continuation of and claims the benefit of U.S. application Ser. No. 12/817,544 filed on 17 Jun. 2010, now U.S. Pat. No. 8,389,041, the disclosure of which is incorporated herein, in its entirety, by this reference.

FIELD OF THE INVENTION

The present invention relates generally to medical devices, and more particular to methods for applying an application material to an implantable device and systems and methods for rotating and coating an implantable device.

BACKGROUND OF THE INVENTION

Percutaneous transluminal coronary angioplasty (PTCA) is a procedure for treating heart disease. This procedure generally entails introducing a balloon catheter assembly into the cardiovascular system of a patient via the brachial or femoral artery and advancing the balloon catheter assembly through the coronary vasculature until the balloon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the balloon catheter assembly to be withdrawn from the vasculature.

While PTCA is widely used, it suffers generally from two unique problems. First, the blood vessel may suffer acute occlusion immediately after or within the initial hours after the dilation procedure. Such occlusion is referred to as "abrupt closure." Abrupt closure occurs in approximately five percent of cases in which PTCA is employed. The primary mechanisms of abrupt closures are believed to be elastic recoil, arterial dissection, vasospasm, and/or thrombosis. The second problem associated with this procedure is the re-narrowing of an artery after an initially successful angioplasty. This re-narrowing is referred to as "restenosis," which typically occurs within the first six months after angioplasty. Restenosis is believed to be due to, among other things, the proliferation and migration of cellular components from the arterial wall, as well as through geometric changes in the arterial wall referred to as "remodeling."

To reduce occlusion of the artery, and the development of thrombosis and/or restenosis, an expandable interventional device or prosthesis, one example of which includes a stent, may be implanted in the lumen to maintain the vascular patency. Additionally, to better effectuate the treatment of such vascular disease, it may be preferable to load an intraluminal device or prosthesis with one or more beneficial agents, such as antiproliferatives, for delivery to a lumen. One commonly applied technique for the local delivery of a drug is the use of a polymeric carrier coated onto the surface of a stent. Such conventional methods and products generally have been considered satisfactory for their intended purpose.

However, implantable devices, such as stents, may be difficult to coat without webbing, cobwebs, or other defects due to their generally intricate geometry. They may also be difficult to uniformly coat (i.e. on the ablumenal, luminal, and sidewall surfaces). Because of these challenges, many commercialized drug eluting stents are being coated by a spray process. However, spray coating may suffer generally from the following: reduced coating speed, reproducibility, and/or coating efficiency (i.e. the amount of material sprayed actually coating the device).

Accordingly, it may be desirable to provide systems and methods for rotating and coating an implantable device.

BRIEF SUMMARY

An embodiment of a method for applying a coating to an implantable device is described. The method includes positioning an implantable device relative to a material delivery apparatus. The implantable device is rotated at a relative speed of more that about 120 revolutions per minute. A spray pattern of an application material is produced using the material delivery apparatus.

In some embodiments, the relative speed is between about 200 revolutions per minute and about 3000 revolutions per minute. In further embodiments, a distance between the implantable device and the material delivery apparatus is between about 1 mm and about 50 mm. In still further embodiments, the implantable device is a stent.

Another embodiment of a method for applying a coating to an implantable device is described. The method includes positioning an implantable device relative to a material delivery apparatus. A spray pattern of an application material is produced using the material delivery apparatus. The implantable device is rotated at a relative speed sufficient to reduce the size of a portion of droplets of the spray pattern.

In some embodiments, the relative speed is generally sufficient to deflect a portion of the droplets of the spray pattern from a first portion of the implantable device toward a second portion of the implantable device. The relative speed, in further embodiments, is generally sufficient to coat at least a portion of an internal surface with application material without increasing a flow rate of the application material. In still further embodiments, the relative speed is generally sufficient to reduce buildup of the application material.

A system for rotating an implantable device is described. The system includes an implantable device having a first longitudinal axis and an inside diameter. The system includes a rotation system configured to rotate the implantable device. The rotation system includes a rotation member having a second longitudinal axis and an outside diameter. The rotation member is rotationally associated with a rotation mechanism. When the first longitudinal axis and the second longitudinal axis are generally parallel, the first longitudinal axis and the second longitudinal axis are offset a desired dimension.

In some embodiments, the desired dimension is between about 0.02 mm and about 1.97 mm. The desired dimension, in further embodiments, is between about 0.3 mm and about 0.5 mm. In still further embodiments, the desired dimension is between about 5% and about 5000% of the outside diameter of the rotation member.

Another embodiment of a system for rotating an implantable device is described. The system includes an implantable device having an inside diameter. The system includes a rotation system configured to rotate the implantable device. The rotation system includes a rotation member having an outside diameter. The rotation member is rotationally associated with a rotation mechanism. The outside diameter of the rotation member is smaller than the inside diameter of the implantable device.

In some embodiments, the inside diameter of the implantable device is between about 0.05 mm and about 2.0 mm. The outside diameter of the rotation member, in further embodiments, is between about 0.03 mm and about 1.7 mm. In still further embodiments, the outside diameter of the rotation member is between about 0.5 mm and about 0.7 mm and the inside diameter of the implantable device is about 1.0 mm.

The outside diameter of the rotation member, in some embodiments, is more than about 5% and less than about 100% of the inside diameter of the implantable device. In further embodiments, the outside diameter of the rotation member is more than about 50% and less than about 70% of the inside diameter of the implantable device.

A further embodiment of a method for rotating an implantable device is described. The method including positioning a generally annular implantable device having an inner surface relative to a rotation member having an outer surface such that less than the entire inner surface of the implantable device and less than the entire outer surface of the rotation member are in general contact with each other. A rotational force is applied to the rotation member, such that the rotation member begins to rotate at a specified rotation speed causing at least a portion of the outer surface of the rotation member to apply a frictional force to at least a portion of the inner surface of the implantable device.

In some embodiments, the frictional force between the rotation member and the implantable device causes the implantable device to rotate at a speed corresponding to the specified rotation speed of the rotation member. The frictional force between at least a portion of the outer surface of the rotation member and at least a portion of the inner surface of the implantable device, in further embodiments, is due to the build up of kinetic energy between at least a portion of the outer surface of the rotation member and at least a portion of the inner surface of the implantable device when the rotation member is rotated relative to the implantable device. In still further embodiments, the frictional force between at least a portion of the outer surface of the rotation member and at least a portion of the inner surface of the implantable device is due to the build up of kinetic energy between at least a portion of the outer surface of the rotation member, at least a portion of the inner surface of the implantable device, and a fluid between at least a portion of the outer surface of the rotation member and at least a portion of the inner surface of the implantable device when the rotation member is rotated relative to the implantable device.

It is to be understood that both the foregoing general description and the following detailed description are exemplary and are intended to provide further explanation of the invention claimed.

The accompanying Figures, which are incorporated in and constitute part of this specification, are included to illustrate and provide a further understanding of the method and system of the invention. Together with the description, the Figures serve to explain the principles of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

Methods and apparatus for rotating and applying a coating to an implantable device are described. Some embodiments of the methods may include rotating an implantable device at a relative speed. The relative speed may include various speeds that may be sufficient to facilitate a reduction in the size of and/or an increase in the spatial resolution of a portion of droplets produced by a material delivery apparatus. An increase in spatial resolution may include an increase in the number of droplets within a volume. Some embodiments of the apparatus may include a rotation system that may rotate an implantable device. The implantable device may be held by a rotation member that may have a smaller diameter than that of the implantable device.

These results, whether individually or collectively, can be achieved, according to one embodiment of the present invention, by employing methods, systems, and/or apparatus as shown in the figures and described in detail below.

Figure 1:
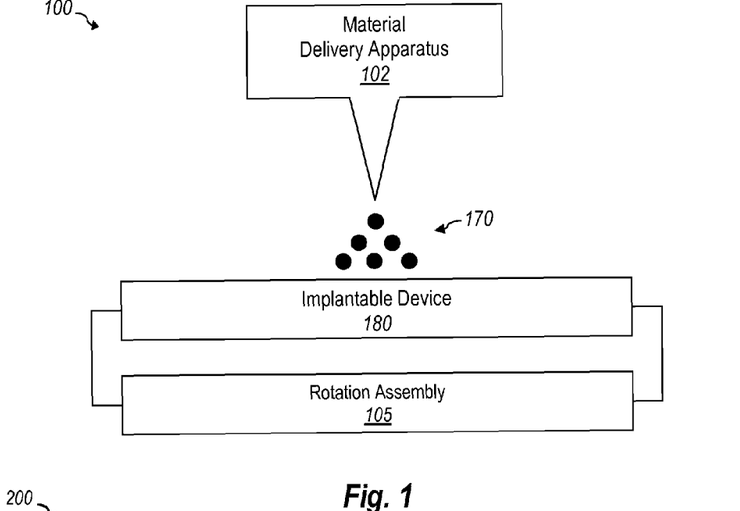
FIG. 1 illustrates a block diagram of an embodiment of a system for rotating and coating an implantable device, in accordance with the present invention.

Turning now to the drawings, FIG. 1 illustrates a block diagram of an embodiment of a system 100 for rotating and coating an implantable device 180, in accordance with the present invention. The system 100 includes a material delivery apparatus 102 that may apply an application material 170 to an implantable device 180. In some embodiments, the material delivery apparatus 102 may include an ultrasonic material delivery apparatus. In further embodiments, the material delivery apparatus 102 may include an ink jet print head. The application material 170 may be applied at a desired spray pressure. In the present embodiment, the spray pressure may be between about 2 psi and about 30 psi. The spray pressure may be varied and/or may be fixed. In embodiments where the material delivery apparatus 102 use an ink jet print head, the spray pressure may be less than 2 psi. For example, the spray pressure may even be approximately zero. The spray pressure may affect the size, velocity, and/or drying rate of at least a portion of the droplets.

The material delivery apparatus 102 may be positioned in a desired location and/or in a desired orientation. For example, the implantable device 180 may be positioned between about 1 mm and about 50 mm from the material delivery apparatus 102 and/or oriented perpendicular to the application 170 material being applied. In some embodiments, the implantable device 180 may be positioned less than about 1 mm from the material delivery apparatus 102. For example, a material delivery apparatus 102 that uses an ink jet print head may be positioned less than about 1 mm from the implantable device 180.

The system 100 may include a rotation system 105. The rotation system may be configured to rotate the implantable device 180. Application material 170 may be applied to the implantable device 180 during rotation. The application material 170 may include beneficial agents, imaging materials, solvents, and/or other application materials.

Beneficial agents may include analgesics, antipyretics, antiasthamatics, antibiotics, antidepressants, antidiabetics, antifungal agents, antihypertensive agents, anti-inflammatories including non-steroidal and steroidal, antineoplastics, antianxiety agents, immunosuppressive agents, antimigraine agents, sedatives, hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, anti-restenosis agents, antipruritics, agents useful for calcium regulation, antibacterial agents, antiviral agents, antimicrobials, anti-infectives, bronchodilators, steroidal compounds and hormones, or combinations thereof. The active agent may include at least one of rapamycin, rapamycin analog, sirolimus, everolimus, zotarolimus, 40-epi-(N1-tetrazolyl)-rapamycin, 40-O-[2-(2-hydroxy)ethoxy]ethyl-rapamycin, Biolimus A9 (Biosensors International, Singapore), deforolimus, AP23572 (Ariad Pharmaceuticals), dexamethasone, dexamethasone acetate, dexmethasone phosphate, momentasone, cortisone, cortisone acetate, hydrocortisone, prednisone, prednisone acetate, betamethasone, betamethasone acetate, prednisone, hydrocortisone, estradiol, acetaminophen, ibuprofen, naproxen, sulidac, heparin, taxol, paclitaxel, and/or combinations thereof.

Imaging materials may include materials, such as radiopaque materials. Examples of radiopaque materials may include high-density materials such as gold, platinum, platinum/iridium, tantalum, tungsten, gadolinium salts, gadolinium complexes, bismuth compounds, barium compounds, and/or other radiopaque materials. As used herein, the term radiopaque may include partial radiopacity as well as total radiopacity.

Solvents may include methanol, ethanol isopropanol, n-propanol, isobutanol, sec-butanol, n-butanol, benzyl alcohol, alcohols, diethyl ether, tetrahydrofuran, 1,4-dioxane, ethers, butyl acetate, isopropyl acetate, ethyl acetate, methyl acetate, esters, acetone, 4-butanone, cyclopentanone, cyclohexanone, ketones, 1-methoxy-2-propanol, diacetone alcohol, methylene chloride, chloroform, carbon tetrachloride, 1,1,1-trichloroethane, trichloroethylene, chlorobenzene, freons, pentane, hexane, cyclohexane, n-heptane, n-octane, benzene, toluene, o-xylene, p-xylene, m-xylene, dimethylenformamide, formamide, dimethylacetamide, dimethylsulfoxide, sulfolane, hexamethyl phosphorustriamide, n-methylpyrrolidone, 1,1,1-trifluoroethanol, hexafluoroisopropanol, water, and/or other solvents.

Other application materials may include polymeric materials comprised of phosphorylcholines, phosphorylcholine linked macromolecules, polyolefins, poly(meth)acrylates, polyurethanes, polyesters, polyanhydrides, polyphosphazenes, polyacrylates, acrylic polymers, poly(lactide-coglycolides) (PLGA), polylactic acids (PLA), poly(hydroxybutyrates), poly(hydroxybutyrate-co-valerates), polydioxanones (PDO), polyorthoesters, polyglycolic acids (PGA), polycaprolactones (PCL), poly(glycolic acid-co-trimethylene carbonates), polyphosphoesters, polyphosphoester urethanes, poly(amino acids), cyanoacrylates, poly(trimethylene carbonate), poly(iminocarbonate), polyalkylene oxalates, polyiminocarbonates, aliphatic polycarbonates, fibrins, fibrinogens, celluloses, starchs, collagens, polycarbonate urethanes, polyisoprenes, polyisobutylenes, polybutadienes, polyethylenes, plasticized polyethylene terephthalates, polyethylene terepthalates, polymethylmethacrylates, ethylene ethylacrylates, polyethyl hexylacrylates, plasticized ethylene vinylacetates, polyvinyl acetates, ethylene vinyl acetates, ethylene vinyl alcohols, polyvinyl alcohols, cross-linked polyvinyl alcohols, cross-linked polyvinyl butyrates, polyvinylbutyrates, polybutylmethacrylates, polyvinyl chlorides, ethylene vinylchloride copolymers, silicones, polysiloxanes, substituted polysiloxanes, polyethylene oxides, polyethylene glycols (PEG), polybutylene terepthalate-co-PEG, PCL-co-PEG, PLA-co-PEG, polyvinyl acetals, polyvinyl acetates, polyamides, polyvinyl pyrrolidones, polyacrylamides, polyvinyl esters, copolymers thereof, polymer derivatives thereof, and/or combinations thereof.

Implantable devices 180 may include endoprostheses, drug delivery stents, drug delivery catheters, stent-grafts, grafts, drug delivery balloons, guidewires, orthopedic implants, PFO closure devices, pacemaker leads, dental implants, fixation screws, indwelling catheters, implantable filters, ocular implants, pharmacotherapeutic implants, blood-contacting components of extracorporeal devices, staples, filters, needles, tubes, coils, wires, clips, screws, sensors, plates, conduits, portions thereof, combinations thereof, and/or other implantable devices.

In one embodiment, the implantable device may include an endoprosthesis for controlling the release of an active agent therefrom. Such an endoprosthesis can include the following: a supporting metal structure configured and dimensioned to be used within a body of a human; a porous body disposed on and at least partially covering the supporting metal structure, the porous body including a first biocompatible material having a plurality of pores; a therapeutically effective amount of an active agent disposed within the pores, the therapeutically effective amount of the active agent being capable of treating and/or preventing a disease; an elution rate controlling matrix disposed within the porous body so as to contain the active agent within the pores, the matrix material including a polymeric biocompatible material that at least partially controls an elution rate of the active agent from the pores; and the pores each having a dimension that is configured to at least partially determine the elution rate.

In one embodiment, the implantable device may include a stent for controlling the release of an active agent therefrom. Such a stent can include the following: a superelastic metal structure configured and dimensioned as a stent to be used within a lumen of an animal; a porous body disposed on and at least partially covering the superelastic metal structure, the porous body including a first biocompatible material having a plurality of pores; a therapeutically effective amount of an active agent disposed within at least a portion of the pores, the therapeutically effective amount of the active agent being capable of treating and/or preventing a disease; and an elution rate controlling matrix disposed on at least one surface of the porous body so as to contain the active agent within at least a portion of the pores, the matrix material including a second biocompatible material that controls an elution rate of the active agent from the pores. Optionally, the porous body is integrated with the supporting structure.

In another embodiment, the implantable device may include an endoprosthesis for controlling the release of an active agent therefrom. Such an endoprosthesis may include a supporting metal structure configured and dimensioned to be used within a body of a human, a coating body disposed on and at least partially covering the supporting metal structure, the coating body including a first biocompatible polymeric material having a largely homogeneous structure, a therapeutically effective amount of an active agent combined with the biocompatible polymeric material to make a largely homogeneous composition, the therapeutically effective amount of the active agent being capable of treating and/or preventing a disease, and the biocompatible polymeric material being either a durable or a biodegradable polymer.

In a further embodiment, the implantable device may include a lumen filter such as a vena cava filter. The lumen filter may include a structure configured and dimensioned as a filter to be used within a lumen of an animal; a porous body disposed on and at least partially covering the structure, the porous body may include a first biocompatible material having a plurality of pores; a therapeutically effective amount of an active agent disposed within at least a portion of the pores, the therapeutically effective amount of the active agent being capable of treating and/or preventing a disease; and an elution rate controlling matrix disposed on at least one surface of the porous body so as to contain the active agent within at least a portion of the pores, the matrix material may include a second biocompatible material that controls an elution rate of the active agent from the pores. Optionally, the porous body is integrated with the supporting structure.

Figure 2:
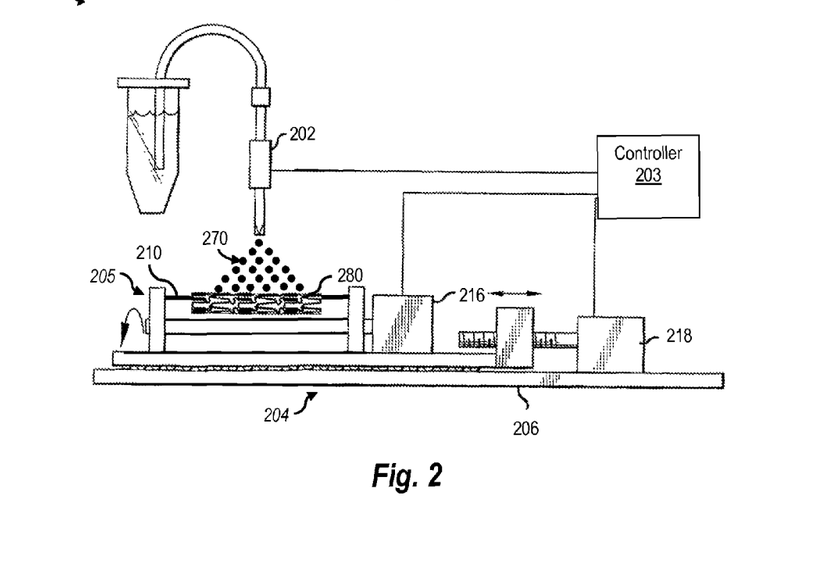
FIG. 2 illustrates a schematic representation of another embodiment of a system for rotating and coating an implantable device, in accordance with the present invention.

FIG. 2 illustrates a schematic representation of an embodiment of a system 200 for rotating and coating an implantable device 280, in accordance with the present invention. The system 200 of this embodiment may be functionally similar to that of the system 100 previously described above and shown in FIG. 1 in most respects, wherein certain features will not be described in relation to this embodiment wherein those components may function in the manner as described above and are hereby incorporated into this alternative embodiment described below. Like structures and/or components are given like reference numerals.

The system 200 may include a material delivery apparatus 202 that may apply an application material 270 to an implantable device 280. The delivery or loading of the application material 270 to the implantable device 280 can be varied through use of a controller 203, the material delivery apparatus 202, a positioning assembly 204, and/or other components. For instance, the controller 203 can be programmed with the structural configuration of the implantable device 280 and control delivery or loading the application material 270 through controlling the operation of the material delivery apparatus 202, the positioning assembly 204, and/or other components.

The positioning assembly 204 can include a driver assembly 206 that creates relative movement between the implantable device 280 and the material delivery apparatus 202. The positioning assembly 204 can also include a rotation assembly 205 that creates rotational movement. The rotation assembly 205 may include a rotation member 210 configured to, at least in part, support and/or rotate the implantable device 280.

As mentioned above, the controller 203 in communication with the driver assembly 206 can define a dispensing path of relative movement between the material delivery apparatus 202 and the rotation assembly 205. The controller 203 can also communicate with the material delivery apparatus 202 for selectively dispensing application material 270 in a selected format along the dispensing path onto a selected portion of the implantable device 280 supported and/or rotated by the rotation member 210. In one configuration, the rotation assembly 205 supporting and/or rotating the implantable device 280 is longitudinally moveable while the material delivery apparatus 202 remains stationary during dispensing of application material 270. However, in another aspect of the invention the rotation assembly 205 supporting and/or rotating the implantable device 280 may remain longitudinally stationary (although may still rotate) while the material delivery apparatus 202 moves along the dispensing path. Alternatively, both the rotation assembly 205 and material delivery apparatus 202 are longitudinally moveable.

The rotation assembly 205 may be configured to rotate the implantable device 280 at a relative speed. In some embodiments, the relative speed may be between about 30 revolutions per minute and about 3000 revolutions per minute. In one embodiment, the relative speed may be more than about 120 revolutions per minute.

In some embodiments, relative speeds above 3000 revolutions per minute may reduce coating efficiency. In further embodiments, relative speeds below 120 rpm may be insufficient to reduce the size of at least a portion of the droplets. The relative speed may increase with respect to the dimensions of the implantable device 280. For instance, the relative speed may be directly proportional to a dimension (i.e. a diameter, width, other dimension, or combinations of the same) of the implantable device 280.

Rotating the implantable device 280 may include rotating about an axis, generally about an axis (i.e. the axis may move throughout the rotation), rotating about a path, revolving about the rotation member 210, and/or other types of rotation. Rotating the implantable device 280 may also include wobbling, precession, and/or other non-uniform types of rotation.

In another configuration, the system 200 can include a detector or sensor to detect when the material delivery apparatus 202 is aligned with the selected portions of the implantable device 280. Such a detector or sensor can be an optical detector, e.g., linear array detector or infrared detector, ultrasound probe, temperature probe, camera, capacitance meter, electrometer, hall-effect probe, and the like, or any other sensor or detector for detection.

In a further configuration, the system 200 can include a focusing assembly to aid delivery or loading application material 270 through varying or changing the spray pattern of the application material 270. The focusing assembly may include at least one focusing jet, an annular jet, and/or other focusing assembly components.

With continued reference to FIG. 2, the positioning assembly 204 can further include a longitudinal driver 218. The rotation assembly 205 can likewise further include a rotating driver 216. The rotation member 210 may be rotated by the rotation driver 216, which can include a motor. For instance, the rotating driver 216 can be activated to produce a velocity on the implantable device 280 via the rotation member 210 during application material delivery. In some embodiments, the velocity may be a constant angular velocity. Similarly, the longitudinal driver 218 can control advancement of the implantable device 280 longitudinally past the material delivery apparatus 202. Again, the longitudinal driver 218 can include a motor.

Through the system 200, application material 270 can be loaded or delivered to an implantable device 280 in a controlled manner. The system 200 may enable and facilitate relative movement between the material application apparatus 202 and the implantable device 280 to define a dispensing path along which the application material 270 can be selectively dispensed. The positioning assembly 204 and/or rotation assembly 205 may aid the delivery or loading of the application material 270 through varying or changing the spray pattern of the application material 270. Hence, the application material 270 may be selectively dispensed from the material application apparatus 210 to a predetermined portion of the implantable device 280 along the dispensing path.

The dispensing path can include, for example, a sequential series of linear parallel passes that traverse back and forth along one axis of the implantable device 280. The relative motion can be continued in a linear manner between forward and backward or right to left and left to right or upward and downward, depending on the frame of reference. A traversal or a pass can be completed when the relative motion reverses direction. That is, relative motion may continue up to a point on the device or past the implantable device, and then may decelerate, stop, reverse direction, and/or accelerate to a constant velocity. In some embodiments, no deceleration is necessary (i.e. if the motion stops immediately). After each pass, the system 200 may adjust the position of the material delivery apparatus 202 and/or implantable device 280. For example, the relative position of the material delivery apparatus 202 and/or the implantable device 280 may be changed or incremented to limit the possibility of application overlap, although a certain degree of overlap may be permitted.

Alternatively, the dispensing path created by the relative motion of the material delivery apparatus 202 and/or the implantable device 280 can include a single continuous helix that wraps continuously around the body of the implantable device 280 and along the length of the implantable device 280. Alternatively, the dispensing path can include a non-continuous helix.

Figure 3:
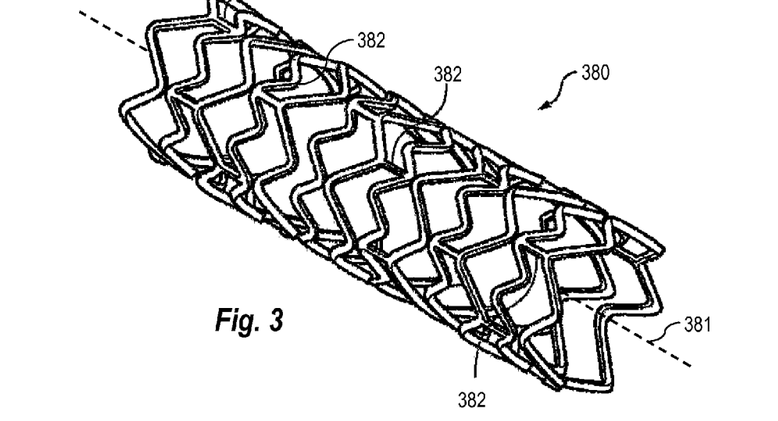
FIG. 3 illustrates an embodiment of an implantable device, in accordance with the present invention.

FIG. 3 illustrates an embodiment of an implantable device 380, in accordance with the present invention. The implantable device 380, in the present embodiment, is a stent. The implantable device 380 may be generally annular and oriented about a longitudinal axis 381. The implantable device 380 may include various struts 382.

Figure 4:
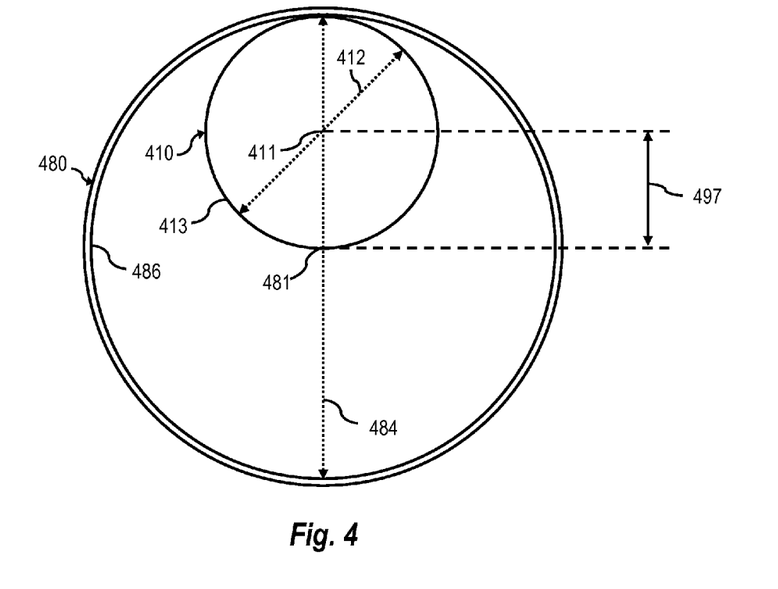
FIG. 4 illustrates a cross-sectional view of an embodiment of an implantable device and a rotation member, in accordance with the present invention.

FIG. 4 illustrates a cross-sectional view of an embodiment of an implantable device 480 and a rotation member 410, in accordance with the present invention. The implantable device 480 and rotation member 410 of this embodiment may be functionally similar to that of the implantable devices 180, 280, 380 and rotation members 210, 410 previously described above and shown in FIGS. 1-3 in most respects, wherein certain features will not be described in relation to this embodiment wherein those components may function in the manner as described above and are hereby incorporated into this alternative embodiment described below. Like structures and/or components are given like reference numerals. For example, in some embodiments, the implantable device 480 may be a stent, such as the implantable device 380 shown in FIG. 3.

The cross-section of the implantable device 480 may be generally annular and may include a longitudinal axis 481, an inside diameter 484, and an inner surface 486 (i.e. ablumenal surface). The cross section of the rotation member 410 may include a longitudinal axis 411, an outside diameter 412, and an outer surface 413. The outer surface 413 of the rotation member 410 may contact, at least partially, the inner surface 486 of the implantable device 480.

The inside diameter 484 of the implantable device 480, in the present embodiment, may range from about 0.05 mm to about 2.0 mm. In other embodiments, the inside diameter 484 may be about 1.0 mm. The outside diameter 412 of the rotation member 410, in the present embodiment, may range from about 0.003 mm and about 1.7 mm. In other embodiments, the outside diameter 412 of the rotation member 410 may range from about 0.5 mm to about 0.7 mm. In further embodiments, other ranges of inside diameter 484 and outside diameter 412 may be used. Ratios of inside diameter 484 and outside diameter 412 may be used. For example, the outside diameter 412 of the rotation member 410 may be more than about 5% and less than about 100% of the outside diameter 412 of the rotation member 410. In another example, the outside diameter 412 of the rotation member 410 may be more than about 50% and less than about 70% of the inside diameter 484 of the implantable device 480. In one embodiment, the rotation member 410 may be a needle.

In the present embodiment, the longitudinal axis 411 of the rotation member 410 and the longitudinal axis 481 of the implantable device 480 are offset by a desired dimension 497. The desired dimension 497 may be selected to increase the "footprint" the outer surface 413 of the rotation member 410 has on the inner surface 486 of the implantable device 480. The "footprint" of the outer surface 413 may affect the amount of friction generated between the rotation member 410 and the implantable device 480.

In some embodiments, the desired dimension 497 may be between about 0.02 mm and about 1.97 mm. In further embodiments, the desired dimension 497 may be between about 0.3 mm and about 0.5 mm. In still further embodiments, the desired dimension may be between about 5% and about 500% of the outside diameter 412 of the rotation member 410.

In one embodiment, less than the entire outer surface 413 of the rotation member 410 may be in general contact with less than the entire inner surface 486 of the implantable device 480. For example, as shown in FIG. 4, only a portion of the outer surface 413 of the rotation member 410 is in contact with the inner surface 486 of the implantable device 480. In addition, the inner surface 486 and/or the outer surface 413 may be non-uniform. For example, the implantable device 380, shown in FIG. 3, may have a non-uniform inner surface. Furthermore, the inner surface 486 and/or outer surface 413 may have varying surface qualities and/or other characteristics that may facilitate rotation of the implantable device 480.

The use of a rotation member 410 may allow rotation of the implantable device 480 without using an interference fit, clamps, and/or other mechanisms for holding the implantable device 480. For example, the rotation member 410 may be rotationally associated with a rotation mechanism, such as the rotation mechanism 216 described in connection with FIG. 2. The implantable device 480 may be rotated at a relative speed (or velocity) by its interaction with the rotation member 410. For example, as a rotational force is applied to the rotation member 410, the outer surface 413 of the rotation member 410 may rotate at a specified rotation speed. The rotation of the outer surface 413 may apply at least a partial frictional force to at least a portion of the inner surface 486 of the implantable device 480.

The frictional force between the outer surface 410 of the rotation member 410 and the inner surface 486 of the implantable device 480 may cause the implantable device 480 to rotate at a speed corresponding to the specified rotation speed of the rotation member 410. The correspondence in rotation speeds may be proportional, in some embodiments. The frictional force between the outer surface 410 of the rotation member 410 and the inner surface 486 of the implantable device 480 may result from a buildup of kinetic energy between at least a portion of the outer surface 413, at least a portion of the inner surface 486, and/or a fluid between at least a portion of the outer surface 413 and at least a portion of the inner surface 486 when the rotation member 410 is rotated relative to the implantable device 480.

Figure 5:
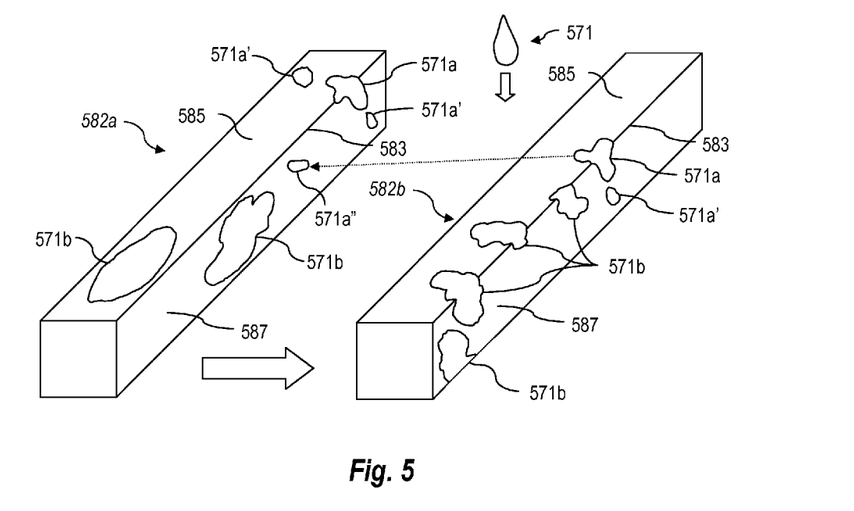
FIG. 5 illustrates a cutaway perspective view of an embodiment of an implantable device having struts and various droplets of an application material, in accordance with the present invention.

FIG. 5 illustrates a cutaway perspective view of an embodiment of an implantable device having struts 582a, 582b and various droplets 571 of an application material, in accordance with the present invention. The struts 582a, 582b of the implantable device of this embodiment may be functionally similar to the struts 382 of the implantable device 380 previously described above and shown in FIG. 3 in most respects, wherein certain features will not be described in relation to this embodiment wherein those components may function in the manner as described above and are hereby incorporated into this alternative embodiment described below. Like structures and/or components are given like reference numerals.

The struts 582a, 582b may include an inner surface (not shown), an outer surface 585, edges 583, side surfaces 587, and/or other edges and/or surfaces. The struts 582a, 582b may be parallel to each other and/or may be oriented in another manner. The struts 582a, 582b may have a square cross-section, a rectangular cross-section, a rounded cross-section, and/or other cross-sectional shapes. In one example, the struts 582a, 582b may be shaped similarly to the struts 382 shown in FIG. 3. The droplets 571 of application material may contact these edges and/or surfaces.

The struts 582a, 582b may move as indicated in FIG. 5. In the present embodiment, the struts 582a, 582b may rotate, i.e. about an axis (not shown). The droplets 571 of application material may also be moving as indicated. In the present embodiment, the droplets 571 may be applied in a direction generally perpendicular to a longitudinal axis (not shown) of the implantable device.

The droplets 571 of the application material may impinge or otherwise contact the struts 582a, 582b. In the present embodiment, some of the droplets 571 may be sheared or otherwise reduced into smaller droplets 571a, 571a', 571a". For example, a droplet 571 may contact an edge 583 of the strut 582b. The droplet 571 may split into smaller droplets 571a, 571a', 571a". In this example, droplet 571a' may contact and coat a portion of the side surface 587, outer surface 586, and edge 583.

Droplets may also be sheared or otherwise reduced without contacting an edge 583 of a strut 582a, 582b. A strut having a rounded cross-section may nevertheless shear and/or otherwise reduce a droplet 571 based on the speed of the strut and/or the droplet 571. Centripetal and/or centrifugal forces may also contribute to the shearing and/or reduction of droplets 571.

A portion of the droplets 571 may be deflected from a first portion of the implantable device toward a second portion of the implantable device. For example, droplet 571a" is shown as being deflected from stud 582b toward (and onto) stud 582a. Deflection of a portion of the droplets from a first portion of the implantable device toward a second portion of the implantable device may be accomplished by rotating the implantable device at a relative speed.

In some embodiments, the relative speed may be sufficient to reduce buildup of the application material. For example, at a relative speed that is not sufficient to reduce buildup of the application material, droplet 571a" may remain on the outer surface 585 of the strut 582b. As these droplets 571a" build up on the strut 572b, defects, such as webbing and/or other defects, may form. By using a sufficient relative speed, these droplets 571a" may not accumulate, but rather may be transferred to other surfaces of the implantable device (i.e. the side surface 587 of strut 582a).

Some droplets 571b may not be sheared or otherwise reduced into smaller droplets. Rather, these droplets 571b may coat a portion of the strut 582a, 582b. Some of these droplets 571b may coat a portion of a single surface, such as the outer surface 585 and/or side surface 587. Other of these droplets 571b may coat portions of multiple surfaces.

Although the inner surface and one side surface of the struts 582a, 582b are not shown, droplets 571 may coat a portion of these surfaces. For example, if the implantable device is generally annular, droplets 571, i.e. either sheared droplets 571a, 571a', 571a" and/or unsheared droplets 571b, may coat a portion of the inner surface (i.e. ablumenal side). In another example, a droplet 571, i.e. either sheared droplets 571a, 571a', 571a" and/or unsheared droplets 571b, may impinge on a portion of the side surface 587 of the strut 582a, 582b near the inner surface and coat a portion of the inner surface and/or side surface 587. In some embodiments, the relative speed may be sufficient to coat a portion of the inner surface with the application material without increasing a flow rate of the application material.

Figure 6:
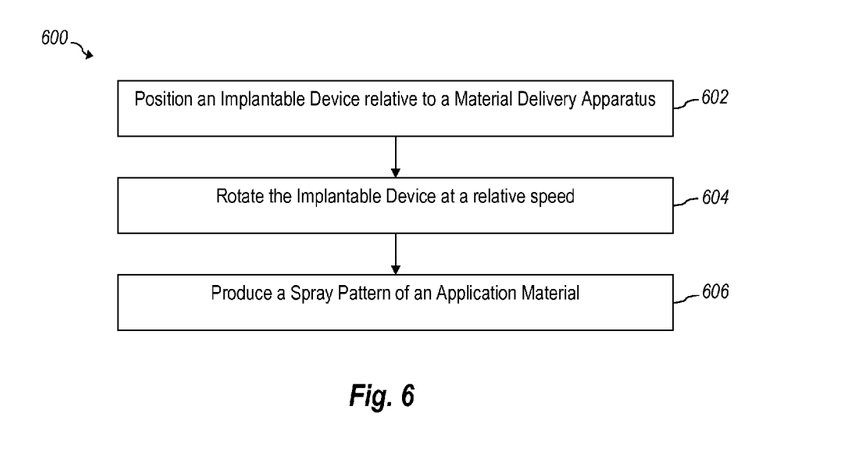
FIG. 6 illustrates an embodiment of a method for rotating and coating an implantable device, in accordance with the present invention.

FIG. 6 illustrates an embodiment of a method 600 for rotating and coating an implantable device, in accordance with the present invention. In the present embodiment, the method 600 may be used in conjunction with the systems 100, 200 and components described in connection with FIGS. 1-5, and/or any other system or components for rotating and coating an implantable device described herein. For example, the rotation system 105 may be used to rotate the implantable device 180.

An implantable device may be positioned relative to a material delivery apparatus, as represented by block 602. Positioning an implantable device relative to a material delivery apparatus may include positioning the implantable device in a desired location and/or in a desired orientation. For example, a stent may be positioned between about 6 mm and about 30 mm from a nozzle of a material delivery apparatus and/or may be oriented perpendicular to the application material being applied.

In some embodiments, before and/or during the application of the application material to the implantable device, an electric charge may be applied to the material delivery apparatus and/or the implantable device. For example, the system component may be charged before applying the application material, but not during the application of the application material. In this example, the system component may nevertheless be charged by virtue of, for example, retaining the charge. In further embodiments, before applying the application material to the implantable device, the material delivery apparatus and/or the implantable device may be grounded.

The implantable device may be rotated at a relative speed, as represented by block 604. The implantable device may be rotated at a relative speed between about 30 revolutions per minute and about 3000 revolutions per minute. Rotating the implantable device at a relative speed may include rotating a rotation member to cause the implantable device to rotate at the relative speed, rotating the implantable device via a holder and/or other device, and/or other methods of rotating the implantable device at a relative speed.

A spray pattern of an application material may be produced, as represented by block 606. Producing a spray pattern of an application material may include directing and/or focusing the spray pattern using, for example, focusing jets.

Rotating the implantable device may include rotating the implantable device at a relative speed sufficient to reduce the size of and/or to increase the spatial resolution of a portion of the droplets of the spray pattern. For example, when the implantable device is rotated at a sufficient relative speed, the struts and/or other portions of the implantable device may shear or otherwise reduce the size of a portion of the droplets of the spray pattern. In another example, when the implantable device is rotated at a sufficient relative speed, the number of droplets in a volume may increase.

Figure 7:
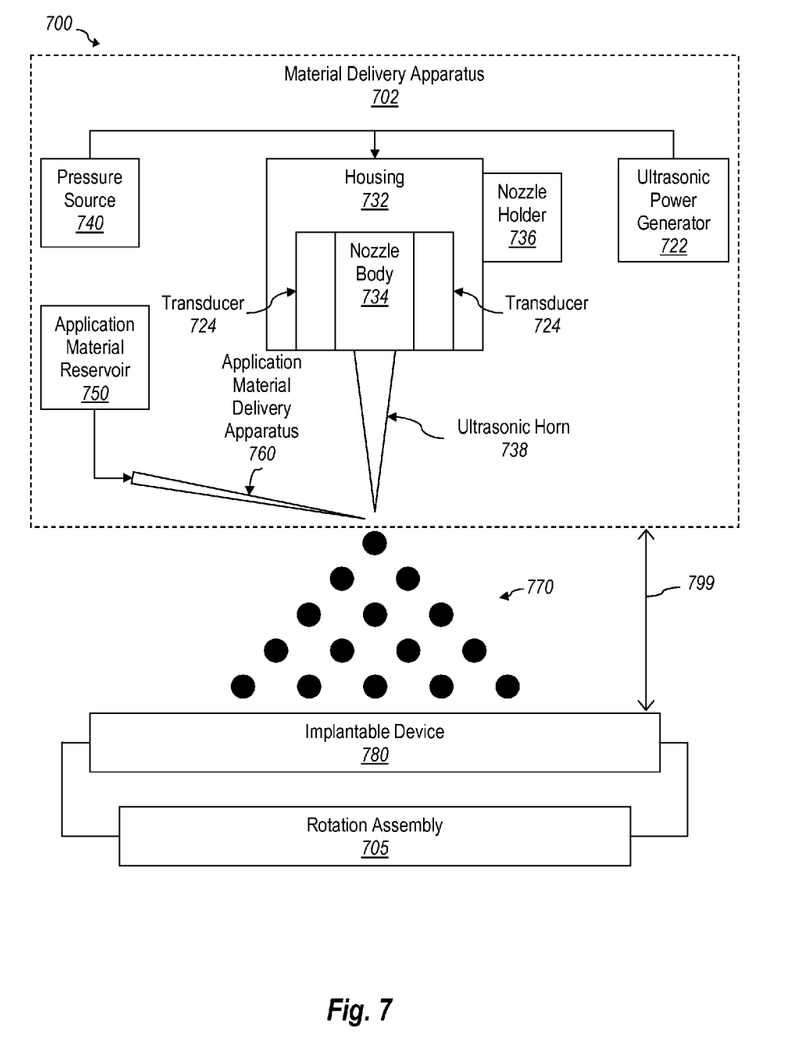
FIG. 7 illustrates a block diagram of a still further embodiment of a system for rotating and coating an implantable device, in accordance with the present invention.

FIG. 7 illustrates a block diagram of a still further embodiment of a system 700 for rotating and coating an implantable device 780, in accordance with the present invention. The system 700 of this still further embodiment may be functionally similar to that of the systems 100, 200 and components previously described above and shown in FIGS. 1-5 in many respects, wherein certain features will not be described in relation to this still further embodiment wherein those components may function in the manner as described above and are hereby incorporated into this alternative embodiment described below.

The system 700 includes a material delivery apparatus 702 that may apply an application material 770 to an implantable device 780 and may include a rotation assembly 705. The material delivery apparatus 702, in the present embodiment, may be an ultrasonic material delivery apparatus that may include an ultrasonic power generator 722, a transducer 724, a housing 732, a nozzle body 734, a nozzle holder 736, an ultrasonic transducer horn 738, a pressure source 740, an application material reservoir 750, and/or an application material delivery apparatus 760.

The system 700, in the present embodiment, may include an ultrasonic generator. The ultrasonic generator may include an ultrasonic power generator 722 and at least one transducer 724. The ultrasonic power generator 722 may generate high frequency electrical energy. High frequency electrical energy may be generated in the range, for example, from about 20 kHz to about 120 kHz. The frequency may be determined based on the characteristics of the nozzle body 734 and/or ultrasonic horn 738.

The ultrasonic power generator 722 may be in electrical communication with at least one transducer 724. The at least one transducer 724 may convert the electrical energy generated by the ultrasonic power generator 722 into mechanical (i.e. vibration) energy. The transducers 724 may include piezoelectric transducers to facilitate in atomizing the application material 770.

The housing 732 may house the nozzle body 734. The housing 732 may be connected to the nozzle holder 736. The nozzle holder 736 may be used to position the material delivery apparatus 702 with respect to the implantable device 780.

In the present embodiment, the material delivery apparatus 702 may include both an application material delivery apparatus 760 and a nozzle body 734 and ultrasonic horn 738. In other embodiments, other configurations may be used. For example, the nozzle body 734 and ultrasonic horn 738 may be in fluid communication with the application material reservoir 750 and a pressure source 740.

The nozzle body 734 and/or the ultrasonic horn 738, in the present embodiment, may be in fluid communication with a pressure source 740. The pressure source 740 may include an air pressure source. The pressure source 740 may generate a pressurized fluid that may be shaped and/or directed by the nozzle body 734 and/or the ultrasonic horn 738. The pressure source 740, in the present embodiment, may generate a low-pressure air stream. In one embodiment, ultrasonic horn 738 may be hollow with the gas from pressure source 740 passing through it.

The application material delivery apparatus 760 may be connected to an application material reservoir 750. The application material reservoir 750 may include a pump, pressurized reservoir, gravity system, and/or other delivery mechanism to direct the application material 770 to the application material delivery apparatus 760. The application material delivery apparatus 760 may include a hypotube. The application material delivery apparatus 760 may deliver the application material 770 to the ultrasonic horn 738 to facilitate atomization of the application material 770. In some embodiments, the application material delivery apparatus 760 may have an electric charge and/or be grounded. In further embodiments, the application material delivery apparatus 760 may be selectively electrically isolated from the ultrasonic power generator 722.

System components may have an electric charge or be grounded. The quantity of electric charge of the charged system components may be generally selected based on a desired application material 770 trajectory. Furthermore, a portion of the system 700 may have a positive or negative charge and/or the system 700 may include a positively or negatively charged conductive member. For example, the components of the system 700 may have a positive or negative charge and/or the system 700 may include a positively or negatively charged conductive member as disclosed in U.S. Provisional 61/015,126, filed Dec. 19, 2007, and entitled "Methods for Applying an Application Material to an Implantable Device", the disclosure of which is hereby incorporated by reference in its entirety.

The implantable device 780 may be rotated and/or held using the rotation assembly 705. The relative speed of the rotation of the implantable device 780 may be determined based on various characteristics of the system 700. For example, the flow rate of the application material 770, the size of the droplets generated by the system 700, the trajectory of the spray pattern, and/or other system characteristics may be considered.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

What is claimed is:

1. A method for applying a coating to an implantable device, comprising:
positioning an implantable device relative to a material delivery apparatus, the implantable device having a first longitudinal axis;
producing a spray pattern of an application material using the material delivery apparatus; and
rotating the implantable device at a speed sufficient to reduce the size of a portion of droplets of the spray pattern and relative to a rotation member upon which the implantable device is disposed, the rotation member having a second longitudinal axis, and when the first longitudinal axis and the second longitudinal axis are generally parallel the first longitudinal axis and the second longitudinal axis are offset at an offset distance.

2. The method of claim 1, wherein the rotational speed of the implantable device is generally sufficient to deflect a portion of the droplets of the spray pattern from a first portion of the implantable device toward a second portion of the implantable device.

3. The method of claim 1, wherein the rotational speed of the implantable device is generally sufficient to coat at least a portion of an internal surface with application material without increasing a flow rate of the application material.

4. The method of claim 1, wherein the rotational speed of the implantable device is generally sufficient to reduce buildup of the application material.

5. The method of claim 1, wherein an outside diameter of the rotation member is between about 0.5 mm and about 0.7 mm and an inside diameter of the implantable device is about 1.0 mm.

6. The method of claim 1, wherein an outside diameter of the rotation member is more than about 5% and less than about 100% of an inside diameter of the implantable device.

7. A method for rotating a stent, the method comprising:
positioning a generally annular stent having an inner surface relative to a rotation member having an outer surface such that less than the entire inner surface of the stent and less than the entire outer surface of the rotation member that is possible of being in general contact with each other are in general contact with each other, the stent having a first longitudinal axis and the rotation member having a second longitudinal axis, and when the first longitudinal axis and the second longitudinal axis are generally parallel the first longitudinal axis and the second longitudinal axis are offset at an offset distance; and applying a rotational force to the rotation member, such that the rotation member begins to rotate at a specified rotation speed causing at least a portion of the outer surface of the rotation member to apply a frictional force to at least a portion of the inner surface of the stent and rotate the stent relative to the rotation member.

8. The method of claim 7, wherein the frictional force between the rotation member and the stent causes the stent to rotate at a speed corresponding to the specified rotation speed of the rotation member.

9. The method of claim 7, wherein the frictional force between at least a portion of the outer surface of the rotation member and at least a portion of the inner surface of the stent is due to the build up of kinetic energy between at least a portion of the outer surface of the rotation member and at least a portion of the inner surface of the stent when the rotation member is rotated relative to the stent.

10. The method of claim 7, wherein the frictional force between at least a portion of the outer surface of the rotation member and at least a portion of the inner surface of the stent is due to the build up of kinetic energy between at least a portion of the outer surface of the rotation member, at least a portion of the inner surface of the stent, and a fluid between at least a portion of the outer surface of the rotation member and at least a portion of the inner surface of the stent when the rotation member is rotated relative to the stent.

11. The method of claim 7, wherein the offset distance is between about 0.02 mm and about 1.97 mm.

12. The method of claim 7, wherein the offset distance is between about 0.3 mm and about 0.5 mm.

13. The method of claim 7, wherein the offset distance is between about 5% and about 5000% of an outside diameter of the rotation member.

14. The method of claim 7, wherein an outside diameter of the rotation member is between about 0.5 mm and about 0.7 mm and an inside diameter of the implantable device is about 1.0 mm.

15. The method of claim 7, wherein an outside diameter of the rotation member is more than about 5% and less than about 100% of an inside diameter of the implantable device.

* * * * *